US 8,298,249 B2

(12) United States Patent
Onuki et al.

(10) Patent No.: US 8,298,249 B2
(45) Date of Patent: Oct. 30, 2012

(54) MEDICAL LIGATING APPARATUS

(75) Inventors: Yoshio Onuki, Hino (JP); Satoshi Miyamoto, Nishitama-gun (JP); Koichi Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 1159 days.

(21) Appl. No.: 11/643,582

(22) Filed: Dec. 21, 2006

(65) Prior Publication Data

US 2007/0106309 A1  May 10, 2007

Related U.S. Application Data

(63) Continuation of application No. 10/341,762, filed on Jan. 14, 2003, now abandoned.

(30) Foreign Application Priority Data

Jan. 16, 2002   (JP) ................................ 2002-007687

(51) Int. Cl.
*A61B 17/24* (2006.01)
*A61B 17/10* (2006.01)
*A61B 17/04* (2006.01)

(52) U.S. Cl. ....................................... 606/148; 606/113

(58) Field of Classification Search ................. 606/139, 606/144, 170, 113, 110, 138, 148
See application file for complete search history.

(56) References Cited

U.S. PATENT DOCUMENTS

| | | | | | |
|---|---|---|---|---|---|
| 5,196,022 | A | * | 3/1993 | Bilweis | 606/144 |
| 5,693,059 | A | * | 12/1997 | Yoon | 606/139 |
| 5,704,943 | A | * | 1/1998 | Yoon et al. | 606/139 |
| 6,679,892 | B2 | * | 1/2004 | Guido et al. | 606/113 |
| 2003/0167062 | A1 | * | 9/2003 | Gambale et al. | 606/138 |
| 2007/0106308 | A1 | * | 5/2007 | Onuki et al. | 606/139 |

FOREIGN PATENT DOCUMENTS

| | | |
|---|---|---|
| JP | 11-511362 | 10/1999 |
| JP | 2001-502190 | 2/2001 |
| WO | WO 97/09935 | 3/1997 |
| WO | WO 97/30639 | 8/1997 |

OTHER PUBLICATIONS

Two (2) Japanese Office Actions dated Oct. 20, 2009 with translations.

* cited by examiner

*Primary Examiner* — Corrine M McDermott
*Assistant Examiner* — Melissa Ryckman
(74) *Attorney, Agent, or Firm* — Scully, Scott, Murphy & Presser, P.C.

(57) ABSTRACT

A medical ligating apparatus includes a medical ligating device having a member which is made of a flexible line and ligates living tissues, and a fixing member which is movably provided at the ligating member and fixes the living tissues in a ligated state, a manipulating device having a flexible sheath and a proximal manipulating section, and a cutting member for cutting the ligating member. The cutting member is provided on the manipulating device and is movably provided on the ligating member.

10 Claims, 7 Drawing Sheets

MEDICAL LIGATING APPARATUS

CROSS-REFERENCE TO RELATED APPLICATIONS

This application is a continuation application of U.S. Ser. No. 10/341,762 filed Jan. 14, 2003 now abandoned which is based upon and claims the benefit of priority from the prior Japanese Patent Application No. 2002-7687, filed Jan. 16, 2002, the entire contents each of which are incorporated herein by reference.

BACKGROUND OF THE INVENTION

1. Field of the Invention

The present invention relates to a medical ligating apparatus for ligating living tissues by inserting the apparatus into a body in a trans-endoscopic manner.

2. Description of the Related Art

Conventionally, medical ligating apparatuses for ligating a lesion of a living tissue, such as polyp, by inserting the apparatuses through endoscope channels, and inserting them into cavities in a trans-endoscopic manner are known from Jpn. Pat. Appln. KOKAI Publication Nos. 10-194, 10-277046, 11-244294, 48-71090, 8-98840, and 54-30692 and the like. These medical ligating apparatuses are composed of: a sheath that can be inserted through an endoscope channel; a manipulating wire movably inserted through this sheath; a loop shaped ligating wire removably connected to a distal end of this manipulating wire; and a stopper provided at a proximal end of this ligating wire.

In this medical ligating apparatus, when a ligating wire is hooked on a lesion of a living tissue, such as polyp and a manipulating wire is pulled toward a proximal manipulating section side, a stopper moves relatively to the distal end side of the ligating wire. As a result, the loop of the ligating wire is reduced in diameter. Then, the lesion is tightly bound. A blood flow at the lesion is stopped by this ligation, and thus, the lesion tissue necroses and slips off several days later in a ligated state. Then, a ligating device consisting of the ligating wire and the stopper slips off at the same time, and is naturally discharged from the anus.

The ligating wire is formed of, for example, a synthetic resin such as nylon or polyolefin, or alternatively, stainless steel. The stopper is formed of a thin tube consisting of an elastic element such as silicon rubber. In addition, the stopper is a knot formed at a part of the ligating wire as disclosed in Jpn. Pat. Appln. KOKAI Publication No. 48-71090.

After the ligating wire has been tightly bound on the lesion, it is required to isolate the ligating wire and manipulating wire connected to each other. Therefore, as disclosed in Jpn. Pat. Appln. KOKAI Publication No. 48-71090, a scissors is inserted through the endoscope channel, and a proximal end of the ligating wire is cut by the scissors. As disclosed in Jpn. Pat. Appln. KOKAI Publication No. 54-30692, a cutter member is provided at the distal end of a sheath, and a ligating wire is cut by the cutter member.

However, as described previously, after the ligating wire has been tightly bound on the lesion, the scissors is inserted through the endoscope channel in order to isolate the ligating wire and manipulating wire connected with each other. In a manipulation for cutting the proximal end of the ligating wire by the scissors, it is required to replace the medical ligating device with the scissors, and insert it into a body cavity in a trans-endoscopic manner. Thus, there is a problem that an operation time is extended.

In addition, with a structure in which an openable cutter member is provided in the distal end of the sheath as shown in FIG. 7 of Jpn. Pat. Appln. KOKAI Publication No. 54-30692, a large number of parts are required, resulting in higher manufacturing cost. In addition to wires of the ligating device, the manipulating wire for actuating the cutter member is inserted into the sheath. Thus, the sheath is increased in diameter, making it difficult to insert the sheath into an endoscope having a channel with its small internal diameter.

In the case of the cutter member in which a blade oriented in the transverse direction at a proximal end side as shown in FIG. 8 of Jpn. Pat. Appln. KOKAI Publication No. 54-30692 is provided in a cylindrically shaped member, there is a problem that its manufacture is very difficult, and the sheath is increased in diameter.

Further, in the conventional medical ligating apparatuses, the proximal end of the ligating wire is cut, thereby isolating the ligating wire and manipulating wire connected with each other. Thus, the ligating wire remains in the body cavity while this wire is extended from a ligating section. Therefore, for example, interference with another treatment device or endoscope may occur.

BRIEF SUMMARY OF THE INVENTION

It is an object of the present invention to provide a medical ligating apparatus in which a fixing member for fixing living tissues while they are ligated by a ligating member is provided, ligation is carried out by the ligating member, and then, the ligating member can be cut at a proximal end of the fixing member by a series of manipulations.

According to the present invention, there is provided a medical ligating apparatus comprising: a medical ligating device consisting of a ligating member which consists of a flexible wire rod and ligates living tissues, and a fixing member which is movably provided at the ligating member and fixes the living tissues in a ligated state; and a manipulating device having a flexible sheath and a proximal manipulating section, wherein the manipulating device comprises cutting means for cutting the ligating member, the cutting means movably provided on the ligating member and can move back and forth.

According to the present invention, in the medical ligating apparatus, the manipulating device comprises cutting means for cutting the ligating member, the cutting means being movably provided on the ligating member, and the cutting means is advanced and retracted or rotated so that the ligating member can be cut at a proximal end of the fixing member.

Further, according to the present invention, in the medical ligating apparatus, the manipulating device comprises cutting means for cutting the ligating member, the cutting means being movably provided on the ligating member, and the medical ligating device comprises a receiving member for receiving the cutting means, the receiving member being movably provided on the ligating member.

According to the invention, there is provided a medical ligating device, a ligating member which includes a flexible wire rod and ligates living tissues; a fixing member which is movably provided on the ligating member that fixes the living tissues in a ligated state; and cutting means for cutting the ligating member, the cutting means being provided on the fixing member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiment of the invention, and together with the general description given above and the detailed description of the preferred embodiment given below, serve to explain the principles of the invention.

DETAILED DESCRIPTION OF THE INVENTION

Hereinafter, embodiments of the present invention will be described with reference to the accompanying drawings.

Figure 1:
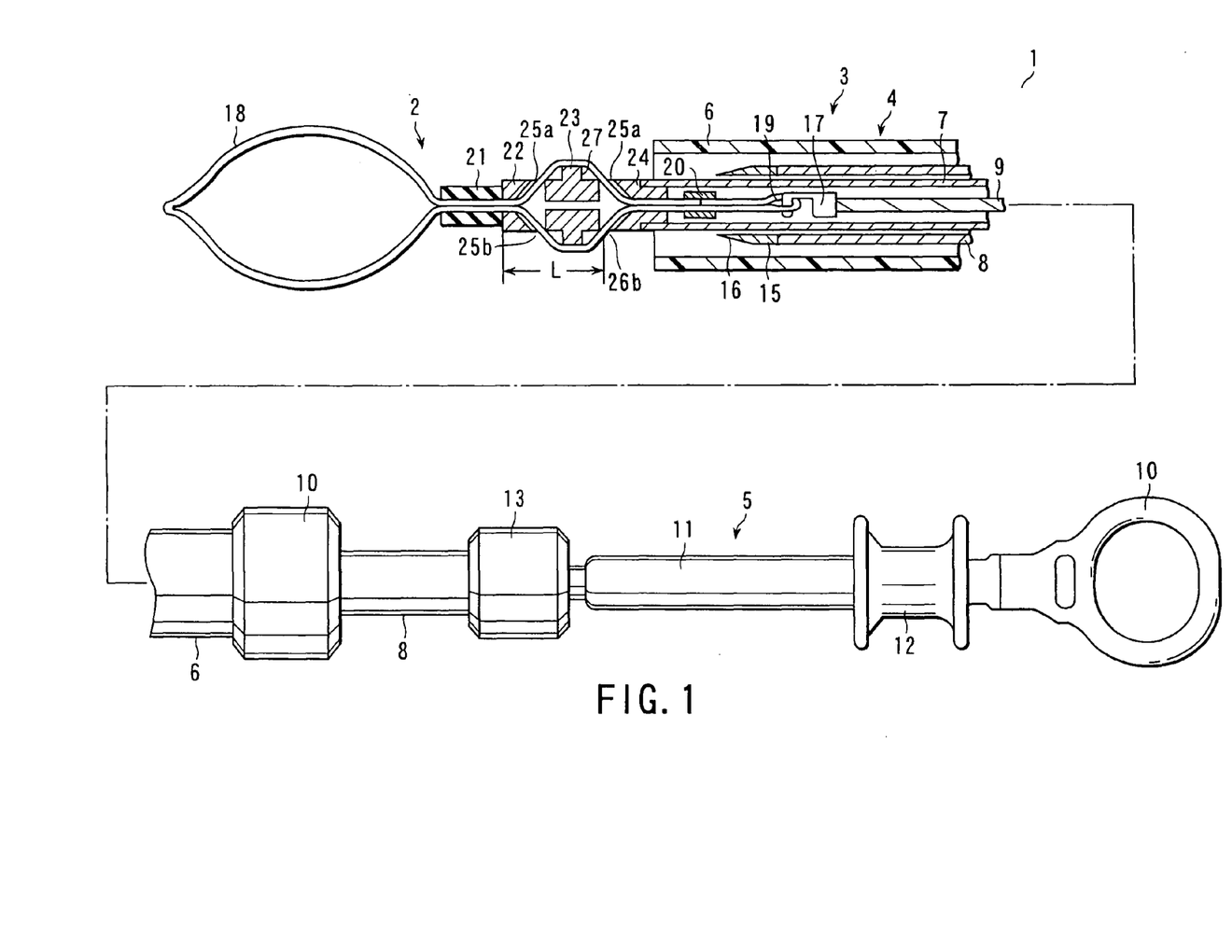
FIG. 1 is a structural view showing an entire medical ligating apparatus according to a first embodiment of the present invention, in which its distal end is cross-sectioned.
Figure 2:
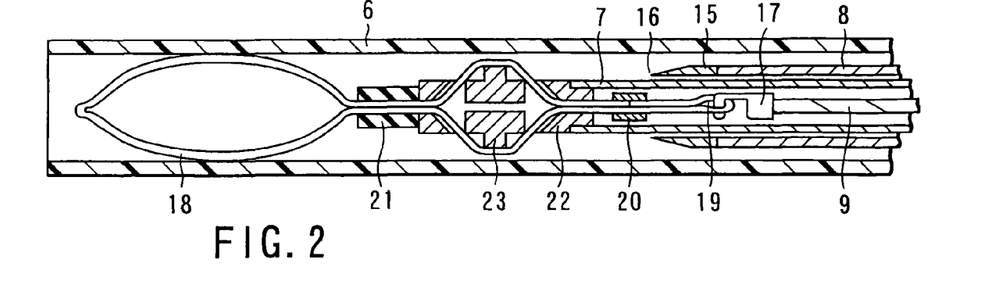
FIG. 2 is a longitudinal side cross section showing a distal end of the medical ligating apparatus according to the first embodiment.
Figure 3:
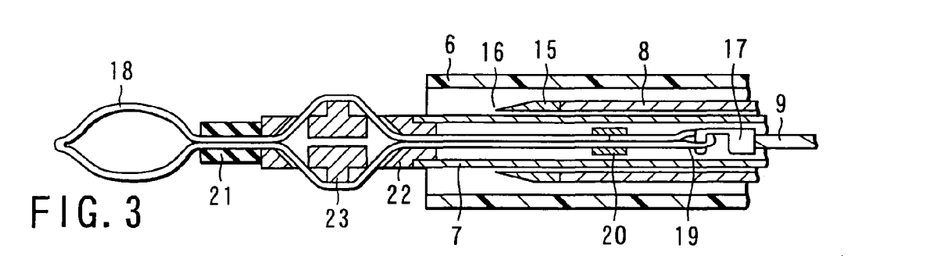
FIG. 3 is a longitudinal side cross section showing a distal end of the medical ligating apparatus according to the same embodiment.
Figure 4:
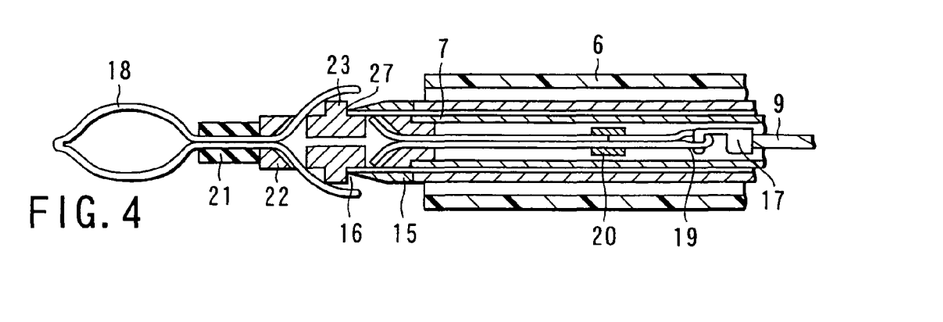
FIG. 4 is a longitudinal side cross section showing a distal end of the medical ligating apparatus according to the first embodiment.
Figure 5:
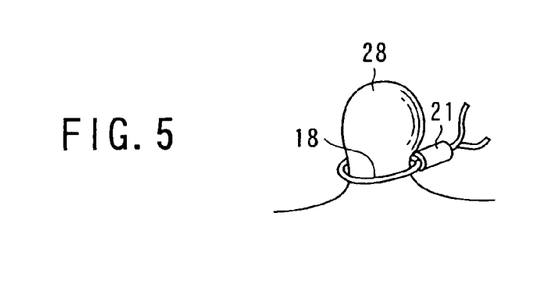
FIG. 5 is a perspective view showing a state in which a lesion is ligated by a ligating wire according to the first embodiment.

FIG. 1 to FIG. 5 show a first embodiment of the present invention. FIG. 1 is a structural view showing an entire medical ligating apparatus, in which its distal end is cross-sectioned. FIG. 2 to FIG. 4 are longitudinal side cross sections of the distal end. FIG. 5 is a perspective view showing a state in which a lesion is ligated by a ligating wire.

As shown in FIG. 1, a medical ligating apparatus 1 is composed of: a medical ligating device 2 retained in a living body; and a manipulating device 3 for guiding the medical ligating device 2 into the living body, thereby carrying out ligating manipulation. The manipulating device 3 is composed of: an insert section 4 having flexibility, the insert section being inserted into an endoscope channel; and a proximal manipulating section 5.

The insert section 4 is composed of: an outer sheath 6 that consists of a flexible sheath; an inner sheath 7 that consists of a flexible sheath and is movably inserted into the outer sheath 6 in an axial direction; a cutting sheath 8 engaged with the outer of the inner sheath 7, the cutting sheath being movably inserted in an axial direction; and a manipulating wire 9 that is retractable in an axial direction, the manipulating wire being inserted through the inner sheath 7.

The outer sheath 6 is made of, for example, a plastic having flexibility such as polyethylene or PTFE, and is 2 mm to 5 mm in diameter. In addition, the inner sheath 7 is made of, for example, a plastic having flexibility such as polyethylene or PTFE. A metallic-meshed sheath may be inserted in a plastic sheath. The manipulating wire 9 is formed of a metal twist wire such as stainless steel.

The proximal manipulating section 5 is composed of: a grip 10 fixed to a proximal end of the outer sheath 6; a slider 12 fixed to a proximal end of the manipulating wire 9, the slider being retractable relative to a manipulating section main body 11; a cutting manipulating section 13 fixed to a proximal end of the cutting sheath 8; and a finger hook ring 14. The outer sheath 6, manipulating wire 9, and cutting sheath 8 can be moved relatively in the forward and backward direction by means of the grip 10, slider 12, and cutting manipulating section 13.

At a distal end of the cutting sheath 8, there is provided an annular cutting member 15 made of a metal such as stainless steel, the cutting member serving as cutting means. A sharp cutting blade 16 is provided all around the distal end of the cutting member 15. In addition, a hook shaped engagement member 17 is securely fixed to the distal end of the manipulating wire 9.

Next, a description of the medical ligating device 2 will be given. In the medical ligating device 2, there is provided a loop shaped ligating wire 18 serving as a ligating member for ligating living tissues at the distal end portion of the device. The ligating wire 18 is formed of a synthetic resin such as nylon or polyolefin, a metal thin wire such as stainless, a silk yarn, or biologically absorptive yarn, and is 0.2 mm to 1 mm in wire diameter. The ligating wire 18 may be in any form of a single wire, twist wire, or knitted wire. In addition, the proximal end side of the ligating wire 18 is folded, and a fold section 19 is formed. Both ends of the ligating wire 18 and the parallel two wires are fixed to an internal cavity of a connecting pipe 20 serving as a fixing parts by means of adhesive bonding or the like.

At the intermediate portion of the ligating wire 18, a tubular stopper 21 serving as a fixing member that is retractable on the wire is movably engaged. The stopper 21 is made of, for example, a rubber such as silicon rubber or fluorine rubber or a variety of thermoplastic elastomers, or a knot of the ligating wire 18. The stopper 21 is advanced, whereby a loop section is reduced in diameter. The stopper 21 is retracted, whereby the loop section is increased in diameter.

A receiving member 22 for receiving the cutting member 15 is provided at the ligating wire 18 at the proximal end of the stopper 21. The receiving member 22 is formed in a cylindrical shape, and is formed of a metal such as stainless or a plastic such as polypropylene, ABS, polyacetal, polycarbonate or the like. An annular protrusion 23 is integrally provided at a substantially intermediate portion in an axial direction. A converging section 24 is provided at the proximal end of the receiving member 22. The converging section 24 is designed so as to be supported after being inserted into the distal end of the inner sheath 7. Therefore, there is no step between an outer periphery face of the inner sheath 7 and an outer periphery face of the receiving member 22 so that the cutting sheath 8 can be advanced and retracted smoothly.

A pair of distal end holes 25a, 25b through which the ligating wire 18 can be inserted are punched at the distal end side more than the annular protrusion 23 of the receiving member 22. A pair of proximal end holes 26a, 26b through which the ligating wire 18 can be inserted are punched at the proximal end side more than the annular protrusion 23. The inner face at the distal end side of the distal end holes 25a, 25b and the inner face at the proximal end side of the proximal end holes 26a, 26b are formed on an incline face so that the ligating wire 18 can be easily inserted and withdrawn. Further, a side face at the proximal end side of the annular protrusion 23 is formed as an abutment face 27 of the cutting member 15.

Each of the folded portions of the ligating wire 18 is led from a proximal opening of the receiving member 22 to the inner of the receiving member 22. Next, these portions each are led from the proximal end holes 26a, 26b to the outer of the receiving member 22. Then, these portions each are led from the distal end holes 25a, 25b to the inner of the receiving member 22 via the outer of the annular protrusion 23. Finally, these portions each are led from the distal opening to the outer. At the distal end side of the receiving member 22, the ligating wire 18 is pressed into an internal cavity of the stopper 21 in a bound state. Further, the full length of the receiving member 22 is about 5 mm to 10 mm. The length of the remaining wire after cut is determined depending on a dimension L between its distal face of receiving member 22 and proximal end holes 26a, 26b each. Thus, the shorter L is desirable, and is set to about 2 mm to 5 mm.

Figure 15:
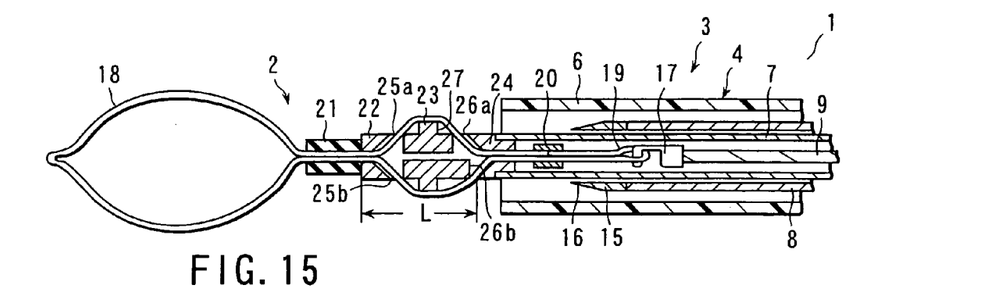
FIG. 15 is a longitudinal side cross section showing a distal end of a medical ligating apparatus showing a modified example of the first embodiment of the present invention.

Now, dimensions of the receiving member 22, annular protrusion 23, and cutting member 15 will be described here. Assume that an external diameter of the receiving member 22 is A, an external diameter of the annular protrusion 23 is B, and an internal diameter of the cutting member 15 is C. These diameters are about 1 mm to 3 mm, and a relationship of A<C, B>C, and B−A=about 0.2 mm to 1 mm is established. In addition, the proximal end holes 26a, 26b, as shown in FIG. 15, may be spaced forwardly or backwardly, respectively.

Now, an operation of the first embodiment will be described here.

First, the slider 12 is manipulated, whereby the manipulating wire 9 is advanced, and the engagement member 17 is protruded from distal openings of the outer sheath 6 and inner sheath 7. In this state, the fold section 19 at the proximal end of the ligating wire 18 is hooked on a hook section of the engagement member 17. When the slider 12 is manipulated, thereby retracting the manipulating wire 9 and introducing the engagement member 17 into the inner of the inner sheath 7, the converging section 24 of the receiving member 22 is supported after being inserted into the distal opening of the inner sheath 7. In this state, when the grip 10 is manipulated, thereby advancing the outer sheath 6, the ligating wire 18 is housed into the inner of the outer sheath 6, and a loop section is reduced in diameter, as shown in FIG. 2.

In this state, the insert section 4 is inserted through the endoscope channel, and is inserted into a body cavity. Then, a distal end of the insert section 4 is guided to a target site in the body cavity. While a lesion 28 such as polyp is observed by means of an endoscope, when the grip 10 is manipulated, thereby retracting the outer sheath 6, the ligating wire 18 is protruded from the distal opening of the outer sheath 6. Then, the loop section of the ligating wire 18 is elastically restored, and is increased in diameter, as shown in FIG. 1.

Next, while the lesion 28 is observed by means of the endoscope, after the loop section of the ligating wire 18 has been hooked on a root of the lesion 28, the slider 12 is manipulated, thereby retracting the manipulating wire 9. Then, the proximal end of the ligating wire 18 is introduced into the inner of the inner sheath 7 via the engagement member 17, and the stopper 21 and receiving member 22 move in a distal end direction of the ligating wire 18. Therefore, the loop section of the ligating wire 18 is reduced in diameter, as shown in FIG. 3, and the lesion 28 is tightly bound. The blood flow to the lesion 28 is stopped by this ligation.

Next, while the slider 12 is held, when the cutting manipulating section 13 is manipulated, thereby advancing the cutting sheath 8, the cutting sheath 8 is advanced while it is guided to the inner sheath 7. Then, the cutting member 15 is engaged with the proximal end of the receiving member 22, and the cutting blade 16 abuts against the abutment face 27. Therefore, the proximal end side of the ligating wire 18 inserted into the receiving member 22 is cut in the vicinity of the proximal end holes 26a, 26b, as shown in FIG. 4.

At this time, the proximal end side of the ligating wire 18 is pulled by the manipulating wire 9, and a tensile stress is applied. Thus, the cutting blade 16 cuts well. In FIG. 4, a time difference may occur without the two top and bottom ligating wires 18 being cut at the same time. However, the two top and bottom ligating wires 18 are connected to each other by means of the connecting pipe 20. Even if these wires are cut one by one, a tensile stress is maintained, and thus, the cutting performance is not degraded.

In the case where the proximal end holes 26a, 26b are displaced forwardly and backwardly, after one of the ligating wires 18 has been cut by the cutting blade 16, the other ligating wire 18 is cut. As a result, both of the ligating wires 18 and the cutting blade 16 do not come into contact with each other at the same time. Thus, the cutting force applied to the ligating wire 18 is not dispersed, and the cutting is made easy.

When the proximal end side of the ligating wire 18 is cut, the inner sheath 7 and receiving member 22 are separated from each other. Then, the ligating device 2 and manipulating device 3 are completely separated from each other. When the insert section 4 is drawn from the endoscope channel, the receiving member 22 slips off from the cut proximal end of the ligating wire 18. Therefore, as shown in FIG. 5, only the ligating wire 18 held in a tightly bound state by means of the stopper 21 is retained in the body, and a surgical operation for tightly binding the lesion 28 completes. The receiving member 22 having slipped off from the ligating wire 18 is naturally discharged to the outer of the body via the digestive tract.

In this way, according to the medical ligating apparatus 1, a manipulation for tightly binding the lesion 28 by the ligating wires 18 and a manipulation of cutting and separating the ligating wires 18 can be carried out in series. Therefore, unlike the prior art, there is no need to replace the ligating apparatus with the scissors in the endoscope channel, and a surgical operation time can be reduced. Moreover, the ligating wire 18 can be cut at a portion close to the stopper 21. Thus, the ligating wire 18 does not remain in the body cavity while being in an expanded state, and interference with another treatment device or an endoscope can be prevented.

Such a simple structure is provided that the cutting means 15 having the cutting blade 16 oriented in the longitudinal direction of the manipulating device 3 is mounted at the distal end of the cutting sheath 8, thus making it possible to reduce the manufacturing cost of the manipulating device and reduce the manipulating device in diameter. Further, even when the cutting performance of the cutting blade 16 is degraded due to repeated use of the manipulating device 3, the cutting sheath 8 and cutting means 15 can be easily replaced by removing them from the manipulating device 3.

Figure 6:
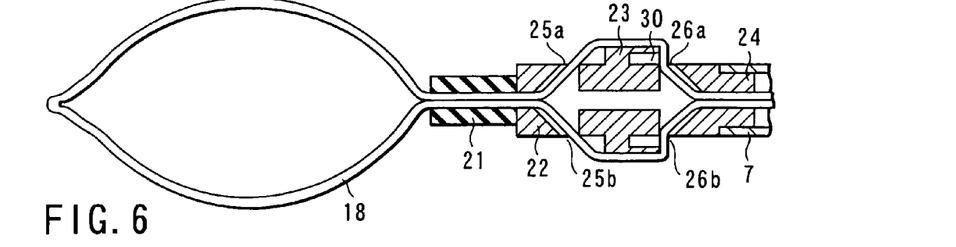
FIG. 6 is a longitudinal side cross section showing a distal end of a medical ligating apparatus according to a second embodiment of the present invention.
Figure 7:
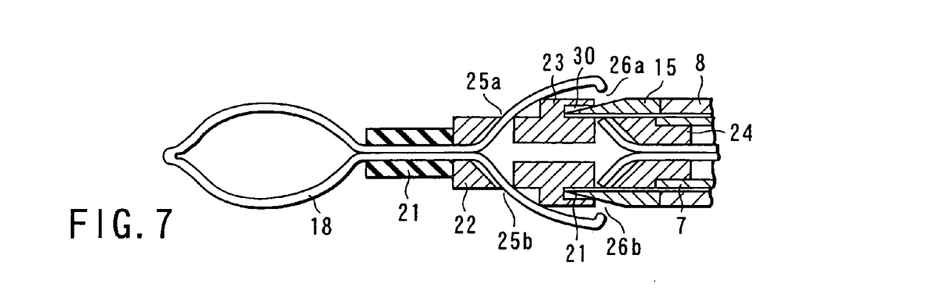
FIG. 7 shows the second embodiment and is a longitudinal, side cross-sectional view of the distal end of the medical ligating apparatus.

FIG. 6 and FIG. 7 show a second embodiment of the present invention. Like elements in the first embodiment are designated by like reference numerals. A duplicate description is omitted here. FIG. 6 and FIG. 7 are longitudinal side cross sections showing a distal end side of a medical ligating apparatus. An annular groove 30 into which the cutting blade 16 of the cutting member 15 is to be inserted is provided on the proximal side face of the annular protrusion 23 of the receiving member 22 according to the present embodiment.

Therefore, while the slider 12 is maintained, when the cutting manipulating section 13 is manipulated, thereby advancing the cutting sheath 8, the cutting sheath 8 is advanced while it is guided to the inner sheath 7. Then, the cutting blade 16 of the cutting member 15 is inserted into the annular groove 30 of the receiving member 22. Therefore, the proximal end side of the ligating wire 18 inserted into the receiving member 22 is cut in the vicinity of the proximal end holes 26*a*, 26*b*, as shown in FIG. 7. At this time, the cutting blade 16 is guided to the annular groove 30, whereby the blade does not slip on the wire, and can cut the wire reliably. In addition, the cutting performance is improved more significantly.

Figure 8:
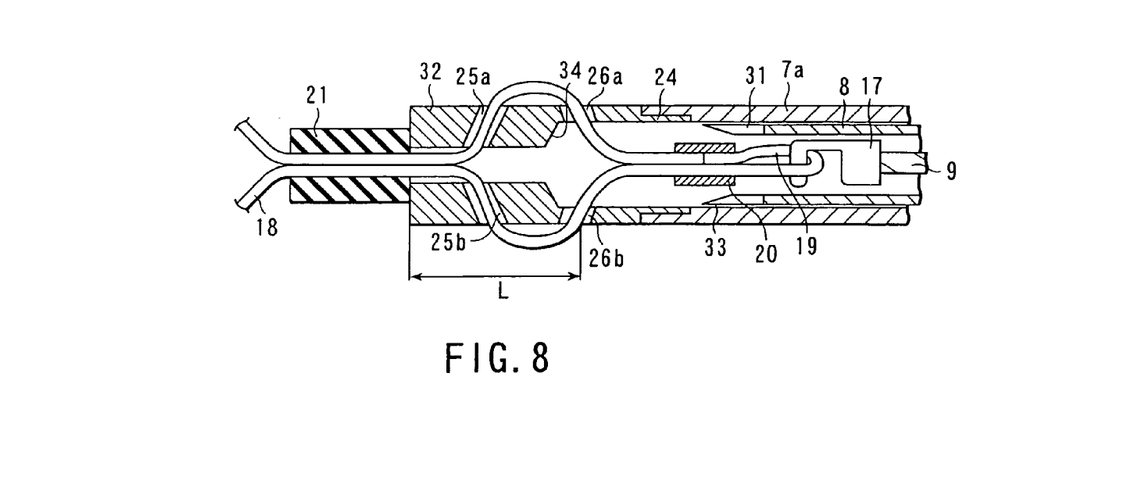
FIG. 8 shows a third embodiment and is a longitudinal, side cross-sectional view of the distal end of the medical ligating apparatus.

FIG. 8 shows a third embodiment of the present invention. Like elements in the first embodiment are designated by like reference numerals. A duplicate description is omitted here. FIG. 8 is a longitudinal side cross section showing a distal end side of a medical ligating apparatus. The cutting member 31 of the present embodiment is provided at the inner of a sheath 7*a* so as to be advanced and retracted by means of the cutting sheath 8. The cutting member 31 may be removable from the cutting sheath 8 so as to facilitate replacement.

In addition, a receiving member 32 is formed in a cylindrical shape that does not have an annular protrusion, and the distal end holes 25*a*, 25*b* and the proximal end holes 26*a*, 26*b* are provided. An abutment face 34 of a cutting blade 33 of a cutting member 31 is provided on an internal wall of the receiving member 32.

Therefore, when the cutting manipulating section 13 is manipulated, thereby advancing the cutting sheath 8, the cutting sheath 8 is advanced while it is guided to the sheath 7*a*. Then, the cutting blade 33 of the cutting member 31 abuts against the abutment face 34 of the receiving member 32. Therefore, the proximal end side of the ligating wire 18 inserted into the receiving member 32 is cut in the vicinity of the proximal end holes 26*a*, 26*b*.

As in the present embodiment, the cutting member 31 is provided at the inner of the sheath 7*a*, whereby any protrusion is eliminated at the outer of the sheath 7*a*, and the cutting blade is not exposed. In this way, the outer sheath is eliminated, and thus, wiring can be directly provided to the endoscope channel. The outer sheath is eliminated, whereby the insert section 4 of the medical ligating apparatus 1 is reduced in diameter, and wiring can be provided to a channel with its small internal diameter.

Figure 9:
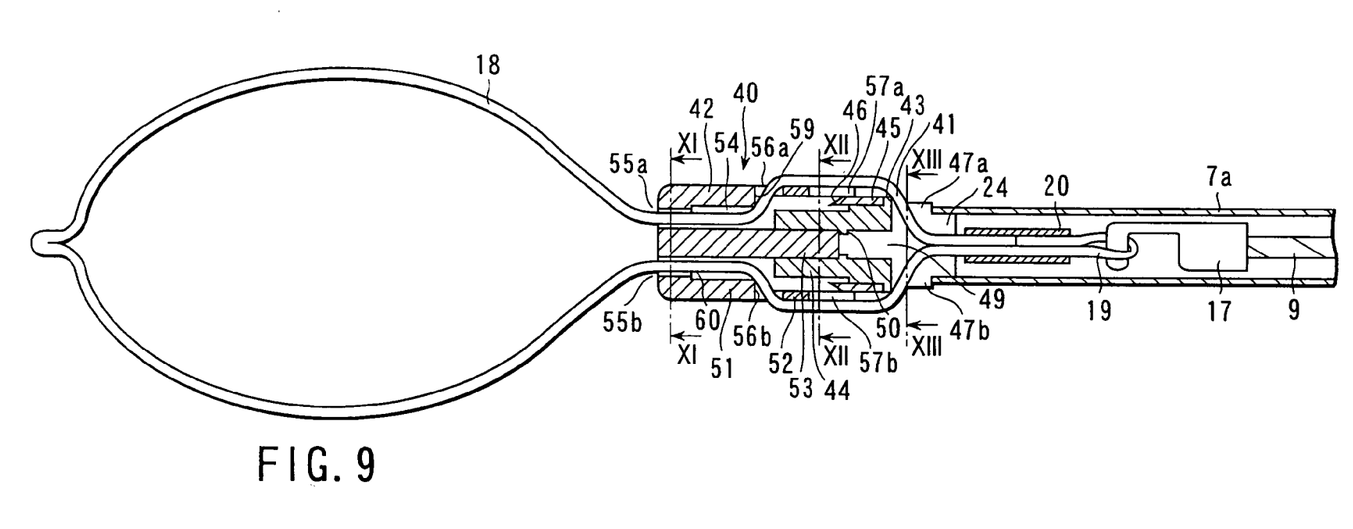
FIG. 9 is a longitudinal side cross section showing a distal end of a medical ligating apparatus according to a fourth embodiment of the present invention.
Figure 10:
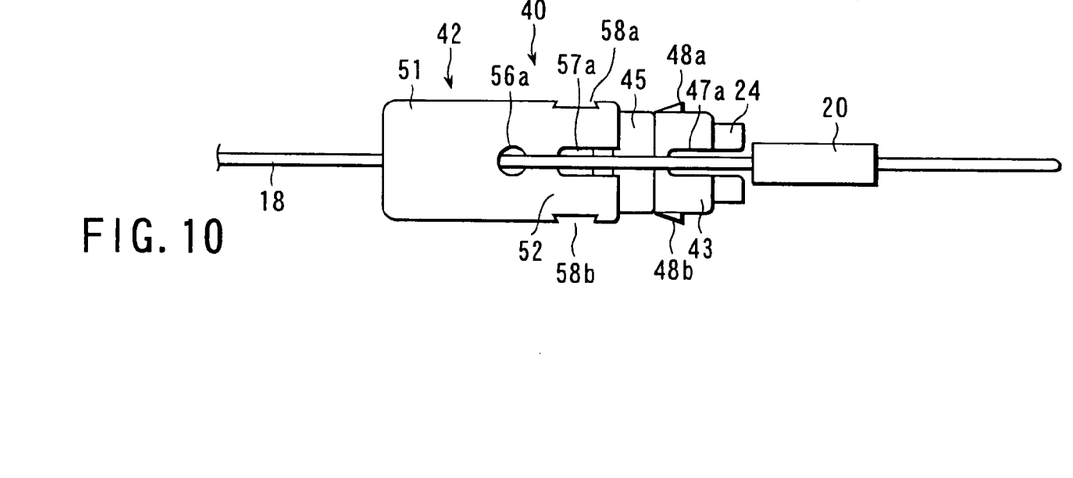
FIG. 10 is a plan view showing a distal end of the medical ligating apparatus according to the fourth embodiment.
Figure 11:
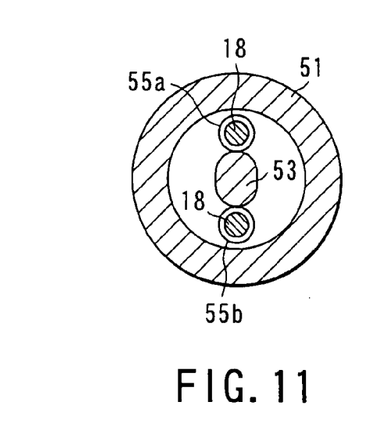
FIG. 11 is a sectional view taken along the line XI-XI of FIG. 9.
Figure 12:
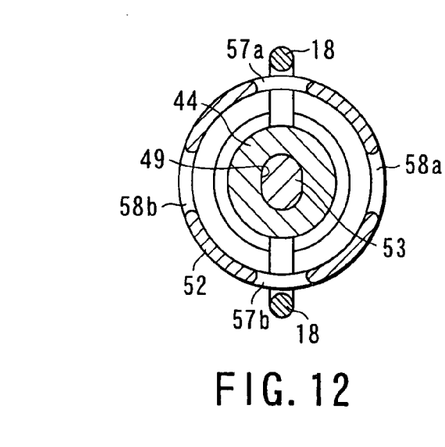
FIG. 12 is a sectional view taken along the line XII-XII of FIG. 9.
Figure 13:
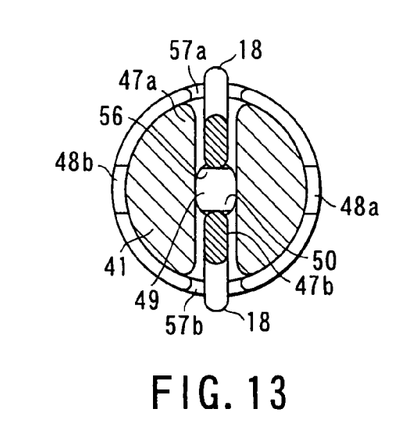
FIG. 13 is a sectional view taken along the line XIII-XIII of FIG. 9.
Figure 14:
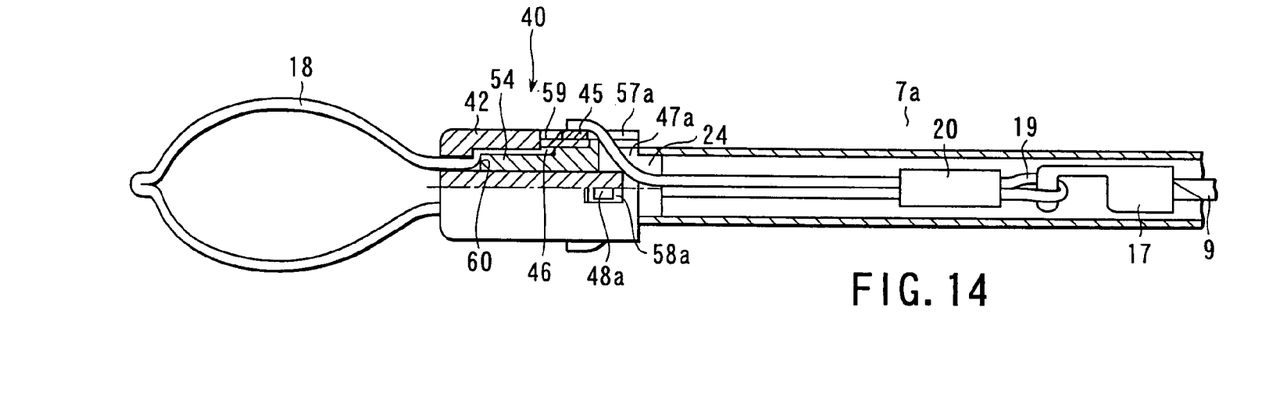
FIG. 14 is a longitudinal side cross section showing a distal end of the medical ligating apparatus in a state in which the ligating wire of the fourth embodiment is cut.

FIG. 9 to FIG. 14 show a fourth embodiment of the present invention. Like elements in the first embodiment are designated by like reference numerals. A duplicate description is omitted here. FIG. 9 is a longitudinal side cross section showing a distal end side of a medical ligating apparatus. FIG. 10 is a plan view showing the same. FIG. 11 is a cross section taken along the line XI-XI. FIG. 12 is a sectional view taken along the line XII-XII. FIG. 13 is a sectional view taken along the like XIII-XIII. FIG. 14 is a longitudinal side cross section showing a distal end side of a medical ligating apparatus in a state in which a ligating wire is cut.

A fixing member 40 is provided at the proximal end side of the ligating wire 18. This fixing member 40 is preferably made of a plastic such as polypropylene, ABS, polyacetal, polycarbonate, or alternatively, a comparatively rigid material with excellent fluidity such as a liquid crystal polymer or polyphthal amide. This member may be made of a metal such as stainless or aluminum, is about 1 mm to 3 mm in external diameter, and is about 5 mm to 10 mm in length.

The fixing member 40 is composed of a first member 41 and a second member 42. The first member 41 is formed in a cylindrical shape. A large diameter section 43 is provided at a proximal end of the first member, and a press-in section 44 consisting of a short diameter section is provided at a distal end thereof. An annular cutting member 45 is engagingly fitted to the outer periphery at the distal end side of the large diameter section 43 while its cutting blade 46 is oriented to the distal end side. Wire guides 47*a*, 47*b* are provided at the top and bottom portions of the outer periphery of the proximal end side of the large diameter section 43. Further, at the outer periphery of the distal end side of the large diameter section 43, engagement claws 48*a*, 48*b* are provided at the right and left parts which are biased by 90 degrees in a peripheral direction relative to the wire guides 47*a*, 47*b*. In addition, at a coaxial section of the first member 41, an internal cavity 49 is provided in an axial direction. A protrusion 50 is provided at the substantially intermediate section in the axial direction of this internal cavity 49. The height of this protrusion 50 is between 0.1 mm to 0.3 mm.

In the second member 42, a columnar section 51 is provided at its distal end, and a cylindrical section 52 is provided integrally with the columnar section 51 at its proximal end. At the center of the columnar section 51, an insert shaft 53 to be inserted into the internal cavity 49 of the first member 41 is protruded through the inner of the cylindrical section 52. Further, a fixing internal cavity 54 into which a press-in section 44 of the first member 41 is to be pressed is provided at the columnar section 51 so as to surround the insert shaft 53. The length of the fixing internal cavity 54 is between 1 mm to 3 mm.

In addition, distal end holes 55*a*, 55*b* into the ligating wires 18 are inserted one by one are provided at the distal face of the second member 42. Side holes 56*a*, 56*b* are provided at the top and bottom parts at the outer periphery of the cylindrical section 52 of the second member 42. Slits 57*a*, 57*b* are provided in the neighborhood of these holes. Further, at the cylindrical section 52, engagement holes 58*a*, 58*b* to be engaged with the engagement claws 48*a*, 48*b* of the first member 41 are provided at the right and left parts which are biased by 90 degrees in a peripheral direction relative to the slits 57*a*, 57*b*. In addition, an abutment face 59 of the cutting blade 46 is provided on an end face at the proximal end side of the columnar section 51 of the second member 42, and an abutment section 60, on which the press-in section 44 abuts, is provided in the vicinity of the distal end of the fixing internal cavity 54. A single-side clearance between an internal diameter of the fixing internal cavity 54 and an external diameter of the press-in section 44 is defined so as to be smaller than an external diameter of the ligating wire 18.

The insert shaft 53 of the second member 42 is inserted into the internal cavity 49 of the first member 41, and a distal face of the insert shaft 53 abuts against the protrusion 50, whereby the insertion depth is restricted. Therefore, the cylindrical section 52 of the second member 42 is engaged with the outer of the cutting member 45 so as to cover the cutting blade 46.

The ligating wire 18 is inserted from the distal end holes 55a, 55b into the inner of the second member 42, and is led out to the outer through the side holes 56a, 56b. Further, the ligating wire 18 is guided by the slits 57a, 57b and wire guides 47a, 47b, and is led to the proximal end side of the fixing member 40. Connection between the fold section 19 of the ligating wire 18 and both of the ends via the connecting pipe 20 is similar to that in the first embodiment.

Next, an operation of a fourth embodiment will be described.

First, the manipulating wire 9 is advanced, whereby the engagement member 17 is protruded from a distal opening of the sheath 7a. In this state, the fold section 19 at the proximal end of the ligating wire 18 is hooked on a hook section of the engagement member 17. When the manipulating wire 9 is retracted, thereby introducing the engagement member 17 into the inner of the sheath 7a, the converging section 24 of the fixing member 40 is supported after being inserted into the distal opening of the sheath 7a. In this state, the sheath 7a including the ligating wire 18 is inserted through the endoscope channel, and is inserted into the body cavity. Then, the distal end of the sheath 7a is guided to a target site in the body cavity. While the lesion 28 such as polyp is observed by means of the endoscope, when the sheath 7a is advanced, the ligating wire 18 is protruded from the distal opening of the channel. Then, the loop section of the ligating wire 18 is elastically restored, and is increased in diameter, as shown in FIG. 9.

Next, while the lesion 28 is observed by means of the endoscope, after the loop section of the ligating wire 18 is hooked on the root of the lesion 28, when the manipulating wire 9 is retracted, the proximal end of the ligating wire 18 is introduced into the inner of the sheath 7a via the engagement member 17. Then, the ligating wire 18 is reduced in diameter, and the lesion 28 is tightly bound.

When the manipulating wire 9 is further retracted, the distal face of the second member 42 of the fixing member 40 abuts against the lesion 28, and the lesion 28 serves as a stopper. Thus, the first member 41 is relatively advanced, and the second member 42 is retracted. Therefore, the insert shaft 53 of the second member 42 breaks the protrusion 50, and is inserted into the internal cavity 49 of the first member 41.

In addition, the press-in section 44 of the first member 41 is advanced in the direction of the fixing internal cavity 54 of the second member 42. Thus, the intermediate section of the ligating wire 18 is fixed to be pinched between an internal face of the fixing internal cavity 54 and an external face of the press-in section 44. Further, when the press-in section 44 of the first member 41 is advanced in the direction of the fixing internal cavity 54 of the second member 42, the cutting blade 46 of the cutting member 45 provided at the first member 41 abuts against an abutment face 59 of the second member 42. Therefore, when the intermediate section of the ligating wire 18 is cut, and a cut end is pinched and fixed between the internal face of the fixing internal cavity 54 and the external face of the press-in section 44.

In addition, when the distal end of the press-in section 44 abuts against an abutment section 60, the engagement claws 48a, 48b of the first member 41 are engaged with the engagement holes 58a, 58b, and the first member 41 is engaged with the second member 42.

The sheath 7a and the fixing member 40 are separated from each other by disconnection of the ligating wire 18, and the ligating device 2 and manipulating device 3 are completely separated from each other. When the sheath 7a is drawn from the endoscope channel, only the ligating wire 18 held in a tightly bound state by means of the fixing member 40 is retained in the body, and a surgical operation for tightly binding the lesion 28 completes.

In this way, according to the medical ligating apparatus 1, a manipulation for cutting and separating the ligating wires 18 at the same time when the lesion 28 is tightly bound by the ligating wire 18 can be carried out in series. Therefore, unlike the prior art, there is no need to replace the ligating apparatus with the scissors in the endoscope channel, and a surgical operation time can be reduced. Moreover, the cut end of the ligating wire 18 is housed at the inner of the fixing member 40, and thus, interference with another treatment device or an endoscope can be prevented more effectively. In addition, the cutting member 45 is provided at the medical ligating device 2 itself. Thus, a new cutting blade is always used without repeated use of the cutting blade 46. As a result, the ligating wire 18 can be cut reliably.

The cutting member 45 is provided at the inner of the fixing member 40, whereby a protrusion is eliminated. Thus, the outer sheath becomes unnecessary, and the wire can be directly inserted through the endoscope channel. The outer sheath becomes unnecessary, whereby the insert section 4 of the medical ligating apparatus 1 can be reduced in diameter, and the wire can be inserted through a channel with its small internal diameter.

Figure 16:
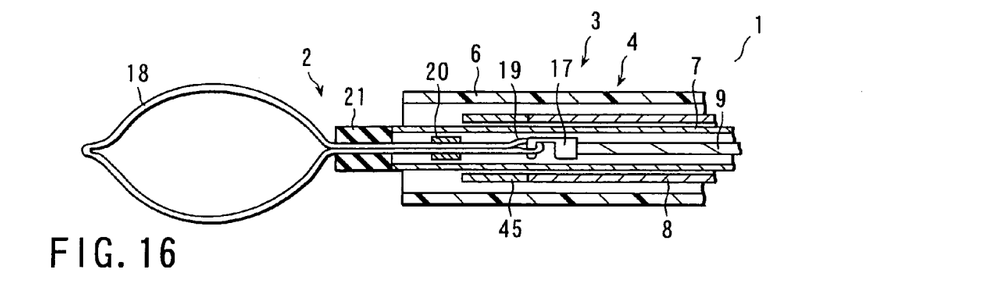
FIG. 16 is a longitudinal side cross section showing a distal end of a medical ligating apparatus according to a fifth embodiment of the present invention.
Figure 17:
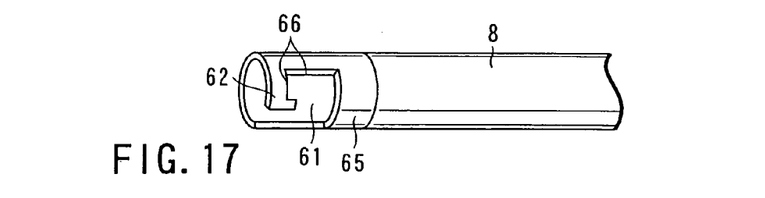
FIG. 17 is an external view showing a distal end of a cutting sheath according to the fifth embodiment.
Figure 18A:
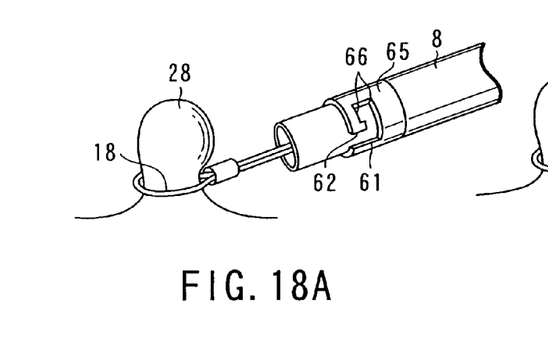
FIG. 18A and FIG. 18B are perspective views showing a state during ligation according to the fifth embodiment.
Figure 18B:
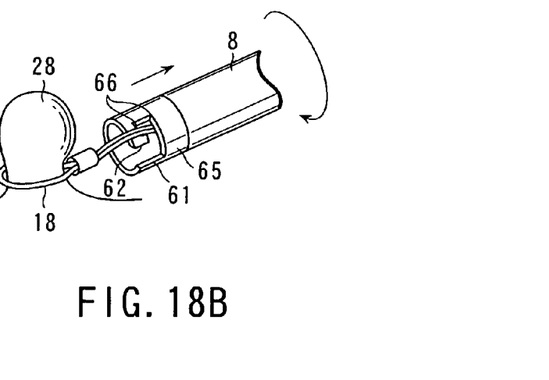

FIG. 16 to FIG. 18 show a fifth embodiment of the present invention. FIG. 16 is a longitudinal side cross section showing a distal end of the apparatus. FIG. 17 is an external view showing a distal end of a cutting sheath. FIG. 18 is a perspective view showing a state during ligation. Only differences from the first to third embodiments will be described here.

As shown in FIG. 16, an external diameter of the stopper 21 is substantially equal to that of the inner sheath 7, and a distal face of the inner sheath 7 can abut against a proximal face of the stopper 21. A cutting sheath 8 is formed of a metallic meshed plastic (for example, polyethylene, PTFE, nylon or the like), or alternatively, a metallic multi-striped coil, and is excellent in rotation tracking properties.

As shown in FIG. 17, a cutting member 65 is connected at a distal end of the cutting sheath 8. The cutting member 65 has a cutout 61. A cutting blade 66 is provided at the distal edge and side face edge of the cutout 61. A claw section 62 is provided at the distal end side of the cutout 61.

Next, an operation of a fifth embodiment of the invention will be described.

After the loop section of the ligating wire 18 has been hooked on the lesion 28, the slider 12 is pulled toward the proximal side, and the lesion 28 is ligated. Then, the slider 12 is slightly pushed and advanced to the distal end side, and a portion of the ligating wire 18 at the proximal end side of the stopper 21 is exposed to the distal end side of the inner sheath 7, as shown in FIG. 18A.

Next the cutting manipulating section 13 is manipulated, whereby the cutting sheath 8 is advanced to be protruded to the distal end side more than the inner sheath 7. In this state, by using a bending manipulation of the endoscope or the like, the ligating wire 18 exposed as shown in FIG. 18B is hooked on a claw section 62.

Then, the cutting manipulating section 13 is pulled to the proximal side or is rotated in the direction shown in FIG. 18B, whereby a cutting blade 66 provided at a cutting member 65 cuts the ligating wire 18 at the proximal end side of the stopper 21.

According to the present embodiment, unlike the first to third embodiments, there is no need to provide a receiving member at the medical ligating device 2, and the number of parts is reduced. Thus the manufacturing cost can be reduced. In addition, the ligating wire 18 does not pass through the distal end holes 25*a*, 25*b* and proximal end holes 26*a*, 26*b* of the receiving member in a bent state, and extends straight between a proximal end of the stopper 21 and the engagement member 17. This makes it possible to push and advance the stopper 21 to the distal end side with a gentle force when the lesion 28 is ligated.

Figure 19:
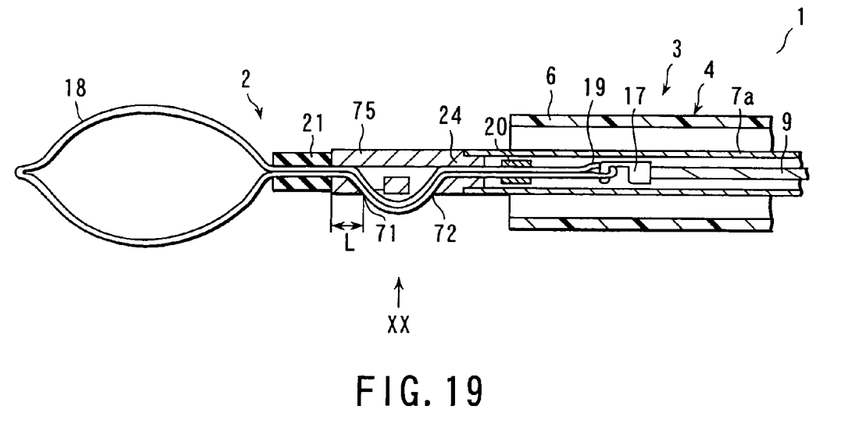
FIG. 19 is a longitudinal side cross section showing a distal end of a medical ligating apparatus according to a sixth embodiment of the present invention.
Figure 20:
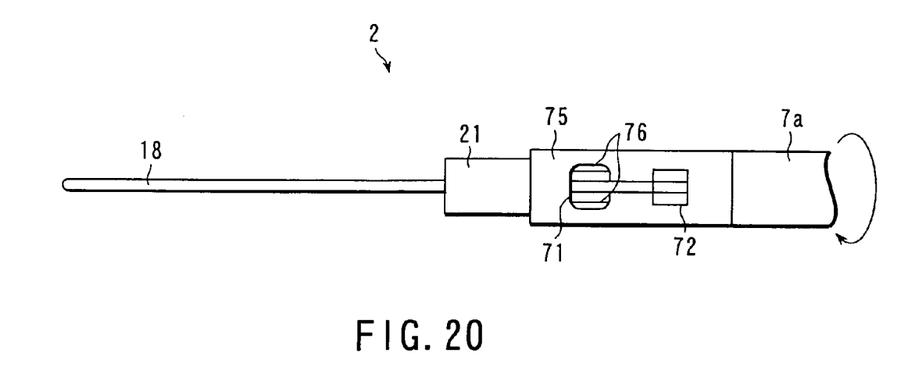
FIG. 20 is an external view showing the apparatus in a direction indicated by the arrow XX in FIG. 19 according to the sixth embodiment.

FIG. 19 and FIG. 20 show a sixth embodiment of the present invention. FIG. 19 is a longitudinal side cross section showing a distal end of the apparatus. FIG. 20 is an external view of the apparatus in the direction indicated by the arrow XX in FIG. 19. Only differences from the first to third embodiments will be described here.

An annular cutting member 75 is provided at the proximal end side of the stopper 21. The cutting member 75 is formed of a metal member such as stainless. A converging section 24 is provided at the proximal end side of the cutting member 75, and is designed to enable engagement with a distal internal cavity of the sheath 7*a*. An external diameter of the converging section 24 is slightly larger than the distal internal diameter of the sheath 7*a*. This external diameter is defined in a dimension such that the cutting member 75, when engaged with the distal internal cavity of the sheath 7*a*, does not slip off easily nor rotate relative to the sheath 7*a*.

In addition, the sheath 7*a* is formed of a metallic meshed plastic (for example, polyethylene, PTFE, or nylon and the like), or alternatively, a metallic multi-stripe coil, and is excellent in rotation tracking properties.

A distal end hole 71 and proximal end hole 72 through which two ligating wires 18 can be inserted are provided on a side face of the cutting member 75. These holes communicate with an internal cavity of the cutting member 75. After the ligating wire 18 has passed through the inner of the stopper 21, the ligating wire enters a distal opening of the cutting member 75. Then, the ligating wire 18 is exposed to the outer through the distal end hole 71. Further, the ligating wire 18 extends to the engagement member 17 through the proximal end hole 72, an internal cavity of the cutting member 75, and an internal cavity of the sheath 7*a*.

It is desirable that a distance L between the distal end of the cutting member 75 and the distal end hole 71 be short. The distance L is set to about 2 mm to 5 mm. In addition, a cutting blade 76 is provided at both edges of the distal end hole 71.

Next, an operation of a sixth embodiment will be described.

After the lesion 28 has been ligated at the loop section of the legating wire 18, the proximal end side of the sheath 7*a* is rotated. The cutting member 75 and the distal end of the sheath 7*a* are engaged with each other so as not to easily rotate therebetween. Thus, the cutting member 75 rotates in unison with the sheath 7*a*.

The distal end side of the ligating wire 18 is fixed to be ligated around the lesion 28. Thus, when the cutting member 75 rotates, the cutting blade 76 abuts against a portion of the ligating wire 18 which is passing through the distal end hole 71, and cuts the portion of the wire. When the manipulating device 3 is removed from the endoscope, the cutting member 75 is taken out of the body while it is fixed to the distal end of the sheath 7*a*.

The cutting blade 76 may be provided at a distal edge of the distal end hole 71. In this case, the sheath 7*a* is pulled to the proximal side, whereby the ligating wire 18 is cut by the cutting blade 76. In this case, the sheath 7*a* and converging section 24 must be set so as not to be disengaged from each other in the range of a force required to cut the ligating wire 18.

According to the present embodiment, the cutting member 75 is provided in place of the receiving members according to the first to third embodiments. As a result, the cutting sheath 8 becomes unnecessary, the number of parts is reduced, and the manufacturing cost can be reduced. In addition, unlike the first to third embodiments, the medical ligating device is not retained in the body in such a state that another member remains at the proximal end side of the fixing member. Thus, interference with another treatment device or an endoscope can be prevented more efficiently immediately after the ligating device has been retained.

As has been described above, a manipulation for tightly binding a lesion by a ligating member and a manipulation for cutting the ligating member can be carried out in series. In addition, there is no need to replace the ligating apparatus with the scissors in the endoscope channel, and a surgical operation time can be reduced. Moreover, the ligating member can be cut at a portion close to the fixing member. Thus, the cut end of the ligating member does not remain in the body cavity while it is extended, and interference with another treatment device or an endoscope can be prevented. In addition, the cutting blade extends in the longitudinal direction of the manipulating device. Thus, the manipulating device can be reduced in diameter. Further, means for cutting the ligating member is formed with a simple structure. Thus, the manufacturing cost can be reduced. Note that the ligating device is not limited to a loop-shaped one.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical ligating apparatus comprising:
a medical ligating device which is adapted to be kept in a body and ligates a target; and
a manipulating device which is operated to introduce the medical ligating device into the body,
wherein the medical ligating device includes;
a flexible line having a proximal end portion, a distal end portion and a middle portion between the proximal end portion and a distal end portion, a ligating section for ligating living tissues being formed by the distal end portion, and an engagement section being provided at the proximal end portion, the middle portion comprising two flexible wire portions,
a fixing assembly provided between the ligating section and the engagement section, the fixing assembly including a first member and a second member provided to be engageable with the first member, the second member being configured to sandwich a part of the middle portion of the flexible line together with the first member and support the part of the flexible line when the second member is engaged with the first member, and a cutting member provided on the first member, the cutting member being configured to cut the middle portion of the flexible line sandwiched between the first and second members when the first and second members are engaged with each other, and wherein the manipulating device includes;

a sheath at least distal end side of which is inserted into the body, a proximal manipulating section being provided on a proximal end side of the sheath, an manipulating wire which is inserted in the sheath, the manipulating wire having an engagement member at its distal end portion, which is engageable with the engagement section of the medical ligating device, and a wire operating device provided on the proximal manipulating section and connected to a proximal end portion of the manipulating wire wherein the first and second members are adapted to be kept in a body in a state that the first and second members support the part of the middle portion of the flexible line which ligates the living tissues.

2. A medical ligating apparatus adapted to ligate living tissues, the medical ligating apparatus comprising:

a medical ligating device which has a ligating section and which is formed of a predetermined elongated material, the medical ligating device that is adapted to be introduced into a body, adapted to ligate the living tissues, and adapted to be kept in a body in a ligate state;

a retracting member to which the medical ligating device is attached for retracting the medical ligating device by a retracting force to ligate the living tissues by the ligating section of the medical ligating device;

a first stopper and a second stopper which oppose each other, with the medical ligating device sandwiched therebetween, which are engaged with each other by relatively moving the first and second stoppers by virtue of the retracting force to lock the medical ligating device in a frictional manner, when the retracting member retracts the medical ligating device, thereby maintaining the ligation state by the medical ligating device; and a cutting member for cutting a portion of the medical ligating device on a proximal end side with respect to a part of the medical ligating device which is frictionally fixed between the first and second stoppers by engagement of the first and second stoppers to keep the medical ligating device in the body, the cutting member being provided to the first stopper and adapted to be kept in the body together with the first and second stoppers after the portion of the medical ligating device is cut;

wherein the cutting member is fixed to the first stopper, and the first stopper is moved toward the second stopper by virtue of the retracting force;

the first stopper includes a cylindrical body having an outer peripheral surface, the second stopper includes a through internal hole defined by an inner peripheral surface, and an intermediate portion of the medical ligating device between the ligating section and the portion to be cut is inserted through the internal hole; and the intermediate portion is sandwiched and locked between the outer peripheral surface of the cylindrical body and the inner peripheral surface of the internal hole of the second stopper.

3. The medical ligating apparatus according to claim 2, wherein:

the second stopper includes a rear end surface, and the cutting member includes a cutting blade oriented to the rear end surface of the second stopper; and the part of the medical ligating device is cut between the rear end surface and the cutting blade when the first stopper is moved toward the second stopper.

4. The medical ligating apparatus according to claim 3, wherein the cylindrical body of the first stopper includes a central hole, and the second stopper includes a central shaft inserted in the internal hole and outwardly extended to insert into the central hole of the cylindrical body to guide the first stopper along the central shaft.

5. A medical ligating apparatus comprising:

an elongate medical ligating device including a rearward section, a ligating section and a forward section between the rearward section and the ligating section, the ligating section being configured to ligate living tissues;

a sheath having a front opening through which the ligating section of the medical ligating device is outwardly extended, the sheath having an elongate axis; and a fixing member which includes a first member having a cutting member, and a second member having an abutting surface, the first and second members being configured to be positioned so that the cutting member and the abutting surface are apart from each other with a first part of the forward section positioned between the cutting member and the abutting surface, wherein the first and second members are configured to be relatively movable along the elongate axis of the sheath into a fixing position so that the cutting member and the abutting surface are approached with each other, thereby fixing a second part of the forward section between the first and second members, and into a cutting position so that the cutting member and the abutting surface are further approached to abut with each other with the second part of the forward section being fixed between the first and second members, thereby cutting the first part of the forward section between the cutting member and the abutting surface.

6. The medical ligating apparatus according to claim 5, wherein the fixing member is configured to be fixed to the opening of the sheath when the first part of the forward section is cut, and to be released from the opening in a state that the ligating section to ligates the living tissues and the second part of the forward section is fixed between the first and second members.

7. The medical ligating apparatus according to claim 5, further comprising an elongate manipulating member which is inserted into the sheath and connected to the rearward section of the medical ligating device to backwardly pull the medical ligating device along the elongate axis so that the ligating section ligates the living tissues and relatively move the first and second members.

8. The medical ligating apparatus according to claim 5, wherein:

the first member includes a first cylindrical body having a central hole extending along the elongate axis and a peripheral surface on which the cutting member is provided, and the second member includes a second cylindrical body having a cylindrical outer part with the abutting surface at one end surface and a central shaft positioned in the cylindrical outer part to defining an annular hole between an inner peripheral surface of the cylindrical outer part and an outer peripheral surface of the central shaft, and the cutting position, the central shaft is inserted into the central hole of the first cylindrical body so the second part of the forward section is fixed between the outer peripheral surface of the first cylindrical body and the peripheral inner surface of the cylindrical outer part.

9. The medical ligating apparatus according to claim 8, wherein the cylindrical outer part of the second cylindrical body includes slits configured to lead the forward section of the medical ligating device onto the outer peripheral surface of the second cylindrical body, and the first cylindrical body includes slits configured to lead the forward section of the medical ligating device into the sheath.

10. The medical ligating apparatus according to claim 9, wherein the cutting member comprises an annular cutting member integrally fitted onto the outer peripheral surface of the first cylindrical body, the annular cutting member having an annular cutting blade oriented to the abutting surface.

* * * * *